United States Patent
Perregaard et al.

(10) Patent No.: US 7,087,801 B2
(45) Date of Patent: *Aug. 8, 2006

(54) PROCESS FOR CATALYTIC SELECTIVE OXIDATION OF A HYDROCARBON SUBSTRATE

(75) Inventors: Jens Perregaard, Gentofte (DK); Gregory Patience, Geneva (CH)

(73) Assignee: Haldor Topsoe A/S, Lyngby (DK)

( * ) Notice: Subject to any disclaimer, the term of this patent is extended or adjusted under 35 U.S.C. 154(b) by 273 days.

This patent is subject to a terminal disclaimer.

(21) Appl. No.: 10/686,680

(22) Filed: Oct. 17, 2003

(65) Prior Publication Data

US 2004/0082671 A1    Apr. 29, 2004

Related U.S. Application Data (63) Continuation of application No. 09/654,558, filed on Sep. 1, 2000, now abandoned.

(60) Provisional application No. 60/152,081, filed on Sep. 2, 1999.

(51) Int. Cl.
C07C 5/333 (2006.01)

(52) U.S. Cl. ............ 585/658; 585/659; 549/233; 562/549; 568/569

(58) Field of Classification Search ........... 585/658, 585/659; 549/233; 562/549; 568/569
See application file for complete search history.

(56) References Cited

U.S. PATENT DOCUMENTS

| | | | |
|---|---|---|---|
| 2,548,875 A | 4/1951 | Degnen | |
| 3,361,839 A | 1/1968 | Lester | |
| 4,405,339 A | 9/1983 | Kunii | |
| 4,827,071 A | 5/1989 | Hazbun | |
| 4,990,714 A | 2/1991 | Nemet-Mavrodin | |
| 5,276,237 A | 1/1994 | Mieville | |
| 5,326,550 A | 7/1994 | Adris et al. | |
| 5,352,610 A | 10/1994 | Braeutigam | |
| 5,601,757 A | 2/1997 | Biselli et al. | |
| 6,515,146 B1 * | 2/2003 | Perregaard et al. | 549/233 |

FOREIGN PATENT DOCUMENTS

| | | |
|---|---|---|
| EP | 0457352 | 11/1991 |
| ES | 2 079 996 | 1/1996 |
| JP | 02078636 A | 3/1990 |
| JP | 0528961 A | 9/1993 |
| JP | 06088590 A | 3/1994 |
| JP | 11090210 A | 3/1999 |

* cited by examiner

*Primary Examiner*—Tam M. Nguyen
(74) *Attorney, Agent, or Firm*—Dickstein Shapiro Morin & Oshinsky LLP (57) ABSTRACT

A reactor system for oxidative conversion of hydrocarbons comprising at least one reactor tube being provided with a plurality of perforations along a wall of the tube and a reaction zone with an active catalyst arranged on tube side and/or shell side of the reactor tube; and a bed of particulates material surrounding the at least one reactor tube, the bed of particulate material being adapted to be fluidised by an oxygen containing atmosphere and to transport heat from the reactor tube.

6 Claims, 6 Drawing Sheets

PROCESS FOR CATALYTIC SELECTIVE OXIDATION OF A HYDROCARBON SUBSTRATE

This is a continuation of application Ser. No. 09/654,558, filed on Sep. 1, 2000, now abandoned which claims the benefit of U.S. provisional application No. 60/152,081, filed Sep. 2, 1999, the entire disclosures of which are incorporated herein by reference.

The present invention relates to selective oxidation of a hydrocarbon substrate. More particular, the invention is directed to oxidation of a hydrocarbon substrate to a corresponding oxidised hydrocarbon compound by reacting the substrate with oxygen in presence of an active catalyst being arranged in an improved reactor system for carrying out the selective oxidation process.

SUMMARY OF THE INVENTION

It is a general object of this invention to provide an improved process and reactor for catalytic oxidation of a hydrocarbon substrate corresponding to an oxidised hydrocarbon compound through controlled addition of oxygen reactant and at high conversion rate and selectivity for the desired oxidised hydrocarbon compound.

In accordance with the above object this invention is a process for the oxidation of a hydrocarbon substrate to a corresponding oxidised hydrocarbon compound by contacting the hydrocarbon substrate with an oxygen containing atmosphere in presence of a catalyst being active in the oxidation of the hydrocarbon substrate, which process comprises the steps of:

passing a process gas containing the hydrocarbon substrate through a reaction zone with the catalyst;

introducing the oxygen-containing atmosphere divided into a plurality of substreams successively into the reaction zone;

within the reaction zone reacting the process gas continuously with the oxygen containing atmosphere; and withdrawing from the reaction zone a product gas containing oxidised hydrocarbon compound and carbon monoxide.

The process will in particular be useful in the selective oxidation of paraffinic and olefinic hydrocarbons and organic hydroxy compounds for the preparation of unsaturated hydrocarbon compounds and oxygenates.

As used herein above and in the following description the term "oxidised hydrocarbon compound" means any hydrocarbon compound resulting from selective oxidation of a hydrocarbon substrate, including alkenes, hydroxy, oxo and carboxyl compounds and acid anhydrides.

A reactor system being useful for carrying out the process according to the invention comprises at least one reactor tube being provided with a plurality of perforations along a wall of the tube and a reaction zone with an active catalyst arranged on tube side and/or shell side of the reactor tube; and a bed of particulate material surrounding the at least one reactor tube, the bed of particulate material being adapted to be fluidised by an oxygen containing atmosphere and to transport heat from the reactor tube.

DETAILED DESCRIPTION OF THE INVENTION

When carrying out the invention in practice, oxygen or oxygen containing atmosphere will be added in controlled manner by successive permeation through a plurality of perforations along wall of a reactor tube.

Tubes with a sufficient number of perforations for the successive addition of oxygen reactant by controlled permeation into the reaction zone may be prepared from metallic or porous ceramic material, either in form of perforated tubes or in form of membranes with a porous structure.

Membrane being useful in the invention are generally prepared by deposition, coating or impregnation of membrane material on surface of a commercially available porous tubular membrane support, such as macroporous aluminium oxide tubes.

The membrane may further be catalytically active when coated or impregnated with catalytically active material.

Suitable catalytic active material for oxidation of the hydrocarbon substrate is known in the art and conventionally employed in the industry.

Those catalytic materials include the known vanadium phosphor oxide compounds (VPO), vanadium on magnesium oxide support (VMgo), vanadium on titan oxide support, molybdates, silver catalysts or supported silver catalysts including mixtures of the above metal compounds.

Figure 1:
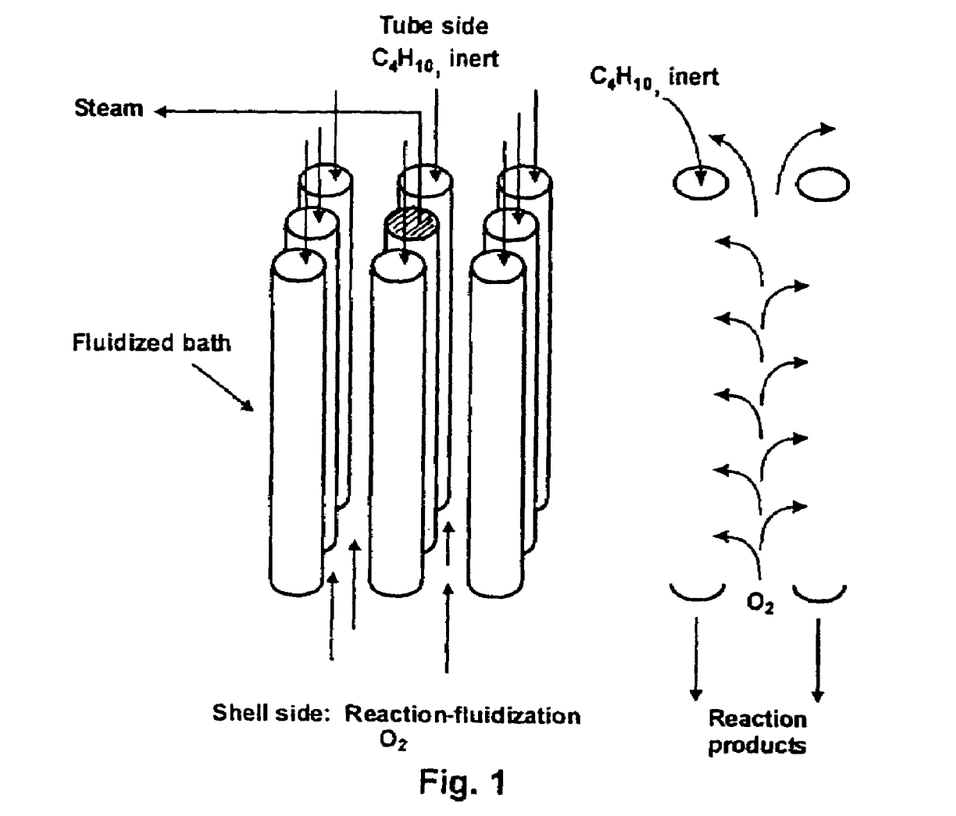
FIG. 1 illustrates a multi-tube reactor immersed in a fluidized bed of sand according to an exemplary embodiment of the present invention.

A multi-tube reactor immersed in a fluidised bed of sand according to a specific embodiment of the invention is shown in FIG. 1.

The reactor comprises a number of perforated reaction tubes with a fixed bed catalyst of conventional vanadium phosphate (VPO) oxidation catalyst arranged on tube side. Cooling tubes arranged within a fluidized bed shell surrounds each reaction tube. A vapor tube carrying steam can be provided.

Figure 2:
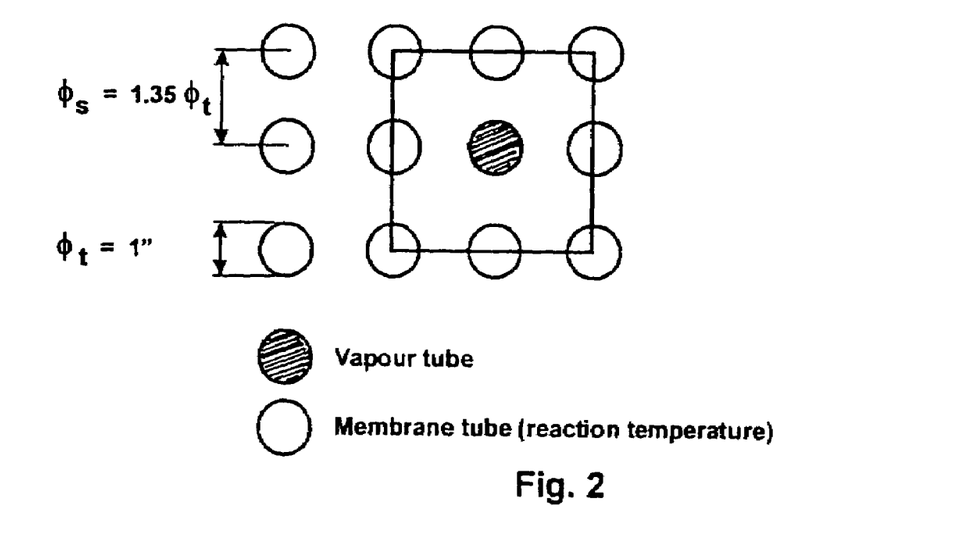
FIG. 2 illustrates schematically an arrangement of tubes in a multi-tube reactor according to an exemplary embodiment of the present invention.

The arrangement of the tubes is schematically shown in FIG. 2. A tubular membrane form the reactor tubes. The shortest centre to centre distance between adjacent tubes is in the shown arrangement 1.35 times the diameter of the tube, and the calculated free section for fluidisation is about 57% of the total area. A filter on the upper side of the reactor avoids intrusion of the solids from the fluidised bed.

As mentioned above and described in more detail below, the reactor tube may be in form of a perforated tube or in form of a porous membrane to provide the desired successive and gradual addition of oxygen to the process gases. The membrane may thereby be formed from inert material (IMR) or catalytic active material (CMR). Useful material for the reactor shell includes carbon steel. The design temperature and pressure are typically about 700° C. and 150 ps, respectively.

The fluidised bed particle could be inert material or catalytic material. The main function of the fluid-bed is as a heat transfer medium.

Use of metallic membranes or perforated metal tubes facilitates necessary welding for the desired final length of a reactor tube and connection between adjacent tubes within the reactor shell.

Figure 3:
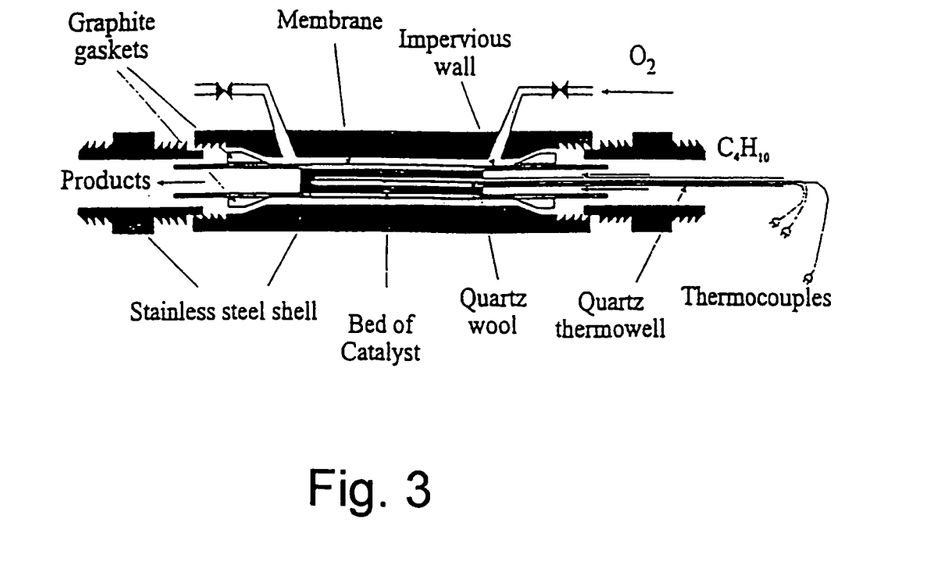
FIG. 3 illustrates a unit for testing a reactor according to an exemplary embodiment of the present invention.

A typical unit for testing a membrane tube is shown in FIG. 3 with a VPO catalyst located inside the membrane tube, plugged with quartz wool, and a stainless steel shell, where the membrane is fixed. Hydrocarbon feed, e.g., butane, is introduced at tube side and oxygen at shell side. Inert gas is introduced with the hydrocarbon feed to the tube side or partly with the oxygen reactant. Graphite gaskets were used to seal the space between the membrane and the shell. Temperature readings are obtained by way of thermocouples received in a thermowell.

In a different embodiment of the IMR test unit as shown in FIG. 3, the VPO catalyst was arranged in the space between the membrane and the stainless steel shell, feeding the butane to the shell side and the oxygen to the tube side and permeating the oxygen outwards. This embodiment is referenced as outward flow reactor (OFR).

The above membrane reactor according to the invention is in particular useful for the selective oxidation of a hydrocarbon surface. The IMR oxygen can be maintained at a sufficient level to avoid decreases in selectivity, but at the same time maintaining the oxygen partial pressure at a level outside of the explosion limits. Since oxygen is fed gradually into the membrane reactor, higher conversion than in the conventional reactor may be obtained. In addition, since no depletion of oxygen at any location in the membrane reactor occurred, changes in the catalyst, which may occur at very low oxygen concentration, can be avoided, and a reasonable level of selectivity can be achieved.

EXAMPLES

EXAMPLE 1

Preparation of an Inert Membrane according to the Invention

Figure 4:
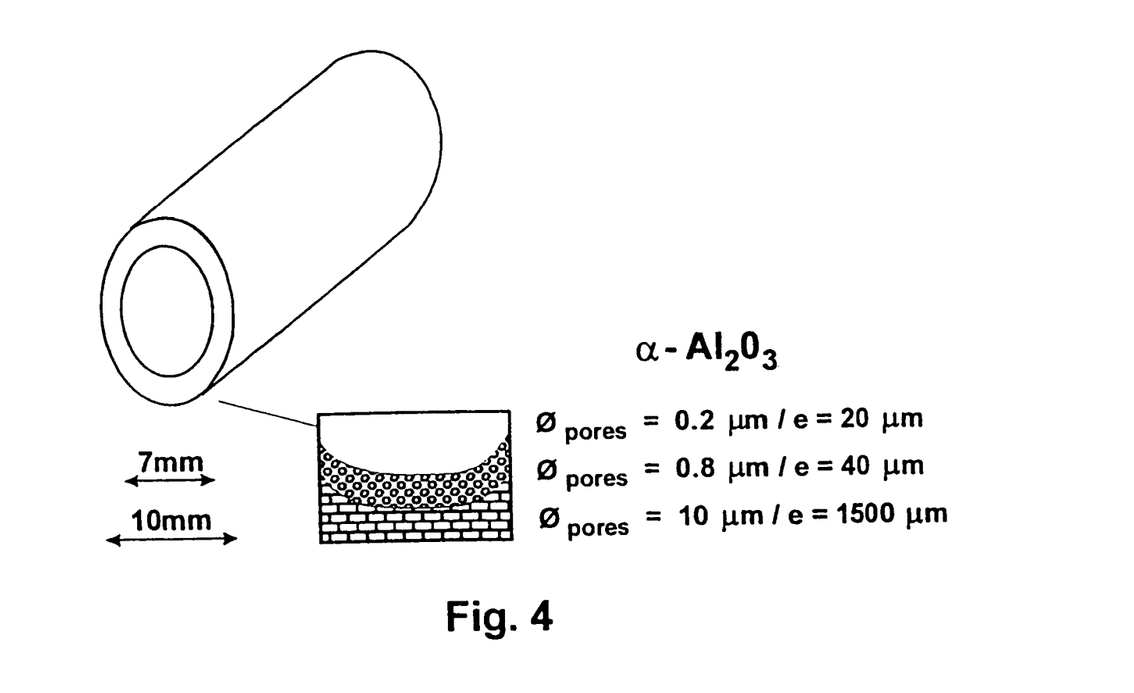
FIG. 4 illustrates a tubular membrane according to an exemplary embodiment of the present invention.

Membranes were deposited in and/or on a 15 cm or 25 cm commercial (SCT) tubular alumina macroporous supports (in/out diameter=7/10 mm) with a sufficient length of enamel at each end. The basic supports have a three layers asymmetric structure with mean pore sizes of 10 µm (external layer), 0.8 µm (intermediate layer) and 0.2 µm (internal layer) (FIG. 4).

Either top-layers or composite membranes were prepared by depositing the membrane material on top of the support or inside its pores (loaded supports), respectively. Thus, the prepared inert membrane has the advantages of i.e. lower influence of defects, a higher thermo-mechanical resistance, a higher reproducibility, and a higher barrier effect due to greater thickness and higher diffusion resistance.

To obtain sufficient membrane stability at reaction conditions (i.e. at 400–500° C.), the membranes were thermally treated at 600° C. or higher, preferably at 800° C. For preparing silica mesoporous membranes, commercial support material was immersed (multiple impregnation) in a commercial silica sol (Ludox A40-Dupont). The impregnated support was dried at 100° C. and calcined at 800° C. The resulting membrane was impregnated with a $LiNO_3$ solution, dried and heated at 600° C. Finally, both ends of the loaded support were enamelled and heated at 800° C. in order to vitrify the ceramic enamel. The prepared membrane was mesoporous with a large pore size distribution (the smaller pore diameters are 4 nm according to porosimetry). The amorphous silica-based materials of this membrane were mainly inside the pores of the macroporous support materials. The membrane gas permeability is a linear function of the trans-membrane pressure and is typically in the range of (15+15 Pm) $10^{-3}$ mole/(sq.Pa.m$^2$), i.e. lower than the permeability of the above-mentioned α-alumina-based membranes. The permeation selectivity at 400–500° C. was lower than the Knudsen selectivity. The silica-loaded membrane was stable after a number of experiments (200 h in the range 400–500° C., with 20 heating-cooling cycles) at industrial operating conditions.

EXAMPLE 2

IMR Preparation

MFI zeolite/α$Al_2O_3$ composite membranes were prepared at 175–190° C. by hydrothermal synthesis of zeolite in/on α-alumina supports in contact with a sol of $SiO_2$/TPAOH/$H_2O$. The template including the pores was eliminated at 600° C. and membranes were treated at 450° C. in $N_2$ overnight before gas permeation tests were conducted.

The quality of the synthesised MFI membranes was first tested by studying the $N_2$ permeability at room temperature as a function of trans-membrane pressure ($\Delta P$). A stable or even slightly decreasing $N_2$ permeability was observed when increasing $\Delta P$ from 0.5 and 3 bars. The membranes were then considered free of macro-defects (>20 nm) because no viscous flow was observed. Permeability was typically within the range from $10^{-8}$ to $10^{-6}$ mol/sq.Pa.m$^2$.

The textural characteristics ($N_2$ adsorption-desorption) of this type of membrane were not modified by calcination at 600° C. for 3 h in wet air (95% humidity). Furthermore, single-gas ($N_2$) permeability behaviour of the membranes was unchanged after more than 20 heating-cooling cycles between room temperature and 500° C. with about 10 hours per cycle in the range of 450–500° C.

EXAMPLE 3

CMR

Sol-gel derived VPO Membrane Materials from the Polymeric Synthesis Route

The synthesis of VPO catalysts was also investigated from alkoxide precursors in organic media in order to increase the specific surface area and $V^{4+}/V^{5+}$-ratio of the VPO membrane materials. A heteroatomic liquid VPO precursor was prepared by reacting di-n-propylphosphate with fresh prepared alkoxide $VO(OR)_3$ in 1-methoxy 2-propanol (ROH). The precipitate was refluxed in ROH, yielding a blue solution, which was used as VPO precursor. The dried VPO precursor was amorphous (XRD) although TEM observations showed presence of small VOHPO$_4$, 0.5H$_2$O crystallites. Different heat treatment have been used for preparation of the polymeric precursor, including thermal treatment in air (T=500, 650° C.), in N$_2$ (T=500° C.), and in a reaction mixture (T=400° C.). XRD, LRS, $^{31}$P, NMR, elemental analysis, and XRD demonstrated that the VPO catalyst obtained at 650° C. in air consisted of VOPO$_4$ microdomains β, γ, δ phases) dispersed in a (VO)$_2$P$_2$O$_7$ pyrophase. The detected presence of the diphosphate phase VO (PO$_3$)$_2$ was consistent with the high molar ratio P/V=1.2 in the catalyst. In all cases, the n—C$_4$ conversion was very low due to the low specific surface area of the catalysts (S$_{BET}$<5 m$^2$/g). As in the aqueous sol gel method, the insertion of 1 wt % cobalt (Co (acac)$_2$) in the starting sol and use of surfactant additives or modifications of the thermal treatments did not improve the specific surface area of the final catalyst.

The above-mentioned blue solution was used for deposition on or impregnation in the alumina tubular support. The membranes were then dried and calcined at 650° C. in air. As described in Example 1, the procedure was repeated typically 5 times until the support reached a stable weight.

Figure 5:
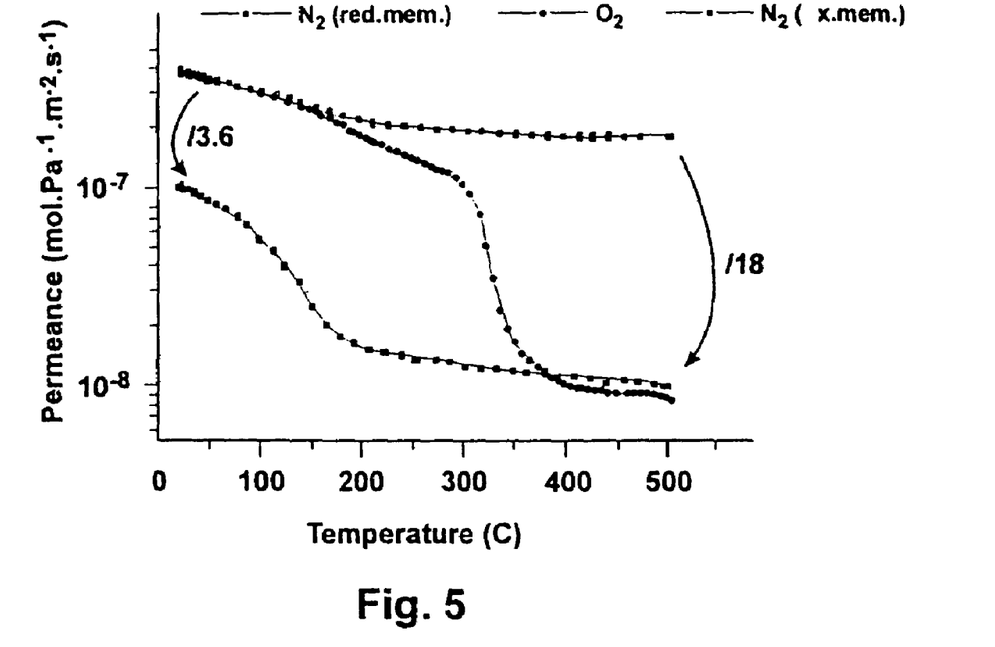
FIG. 5 is a graph comparing thermal evolution of $N_2$ permeability in oxidizing a composite membrane having either an oxidizing treatment or a reducing treatment.
Figure 6:
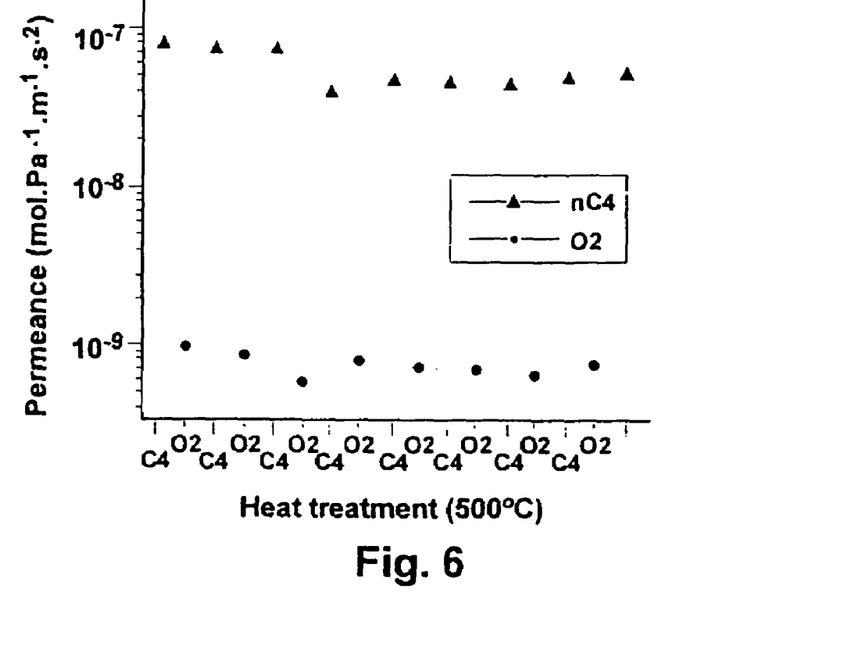
FIG. 6 is a graph showing hydrocarbon and oxygen gas permeability.

The above-prepared composite membranes exhibit an advantageous gas permeability property. FIG. 5 compares thermal evolution of N$_2$ permeability through the VPO/αAl$_2$O$_3$ composite membrane after a reducing treatment (n—C$_4$H$_{10}$ at 500° C.) and after an oxidising treatment (O$_2$ at 500° C.). The ratio of N$_2$ permeability values through the oxidised and reduced membrane is 3.6 at 20° C. and 18 at 500° C. The observed reduction in the N$_2$ permeability through the oxidised membranes was reversible and reproducible, probably due to a modification of the membrane porous texture Nine cycles with n—C$_4$/O$_2$ at 500° C. were performed on a VPO/αAl$_2$O$_3$ membrane. The n—C$_4$H$_{10}$ or O$_2$ single gas permeability (FIG. 6) was measured at 500° C. after 30 min. The next step was to switch off the gas and purge with N$_2$ for 5 min. The reduction-oxidation process was found to be reversible at these conditions. The above type of membrane was reproducible, thermally and chemically stable. The single gas permeability ratio, n—C$_4$H$_{10}$/O$_2$, was about 40 to 500° C.

Figure 7:
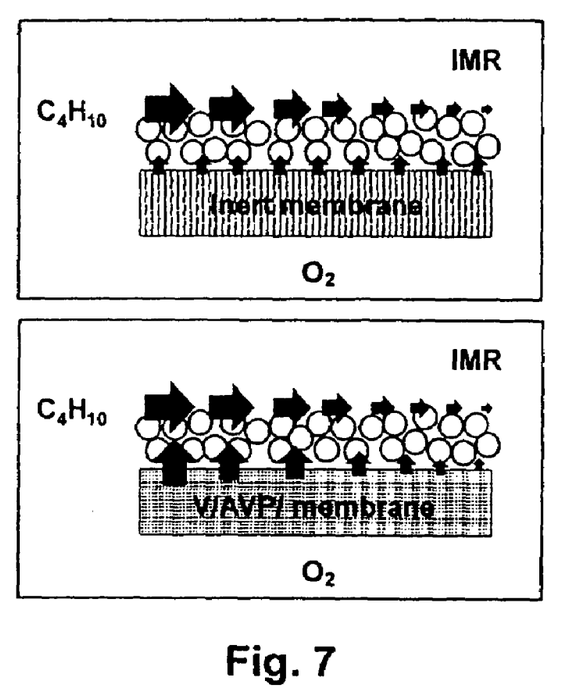
FIG. 7 substantially illustrates gas permeability through a membrane according to an exemplary embodiment of the present invention.

Advantageously, the gas permeability through the membrane is higher when in reduced form and lower in oxidised form, resulting in a self-regulating permeability of O$_2$ through the membrane, controlled oxygen concentration in the IMR (FIG. 7). Depending on the operation conditions such as reactants partial pressure and internal and transmembrane pressures, O$_2$ flow through the membrane was stable after several minutes. If the n—C$_4$H$_{10}$ concentration profile decreased along the reactor (consumption), a non-uniform O$_2$ permeability is obtained by the redox-sensitive membrane, decreasing O$_2$ flow from the inlet to the outlet.

EXAMPLE 4

Metallic Membrane or Flow Distributors

A metallic membrane can be made from sintered metal tubes available from, e.g., Krebsöge. Alternatively, the same effect can be obtained by perforating a metal tube. Preferably, the holes have a diameter between 1–50 μm. Perforations may conveniently be obtained by laser drilling.

EXAMPLE 5

Figure 8:
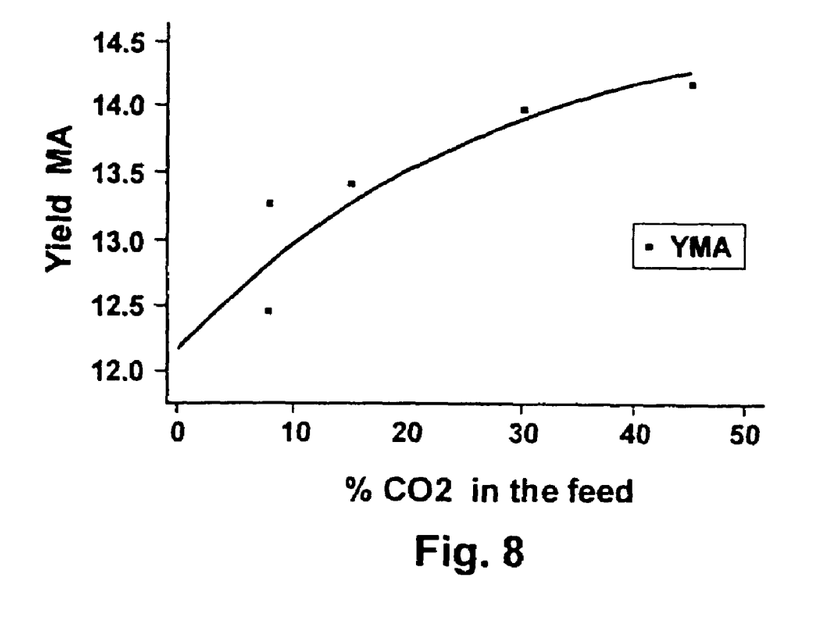
FIG. 8 is a graph showing increased yield from increased $CO_2$ percentage in the feed.
Figure 9:
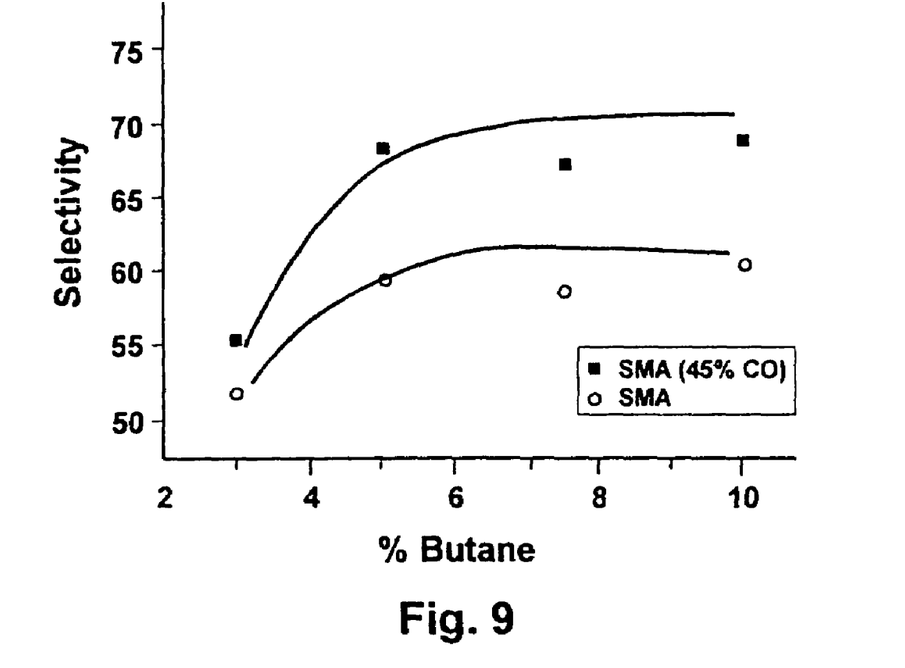
FIG. 9 is a graph showing increased selectivity from an increased percentage of butane according to an exemplary embodiment of the present invention.

Several inert gases including: nitrogen, methane and carbon dioxide were tested. Whereas no changes in reactor performance were observed when methane or nitrogen was employed instead of helium, strong changes were observed with CO$_2$. FIG. 8 shows an increased MA yield when the CO$_2$ percentage in the feed was increased. As obvious from FIG. 9, the effect was stronger when concentration of butane increases.

EXAMPLE 6

Figure 10:
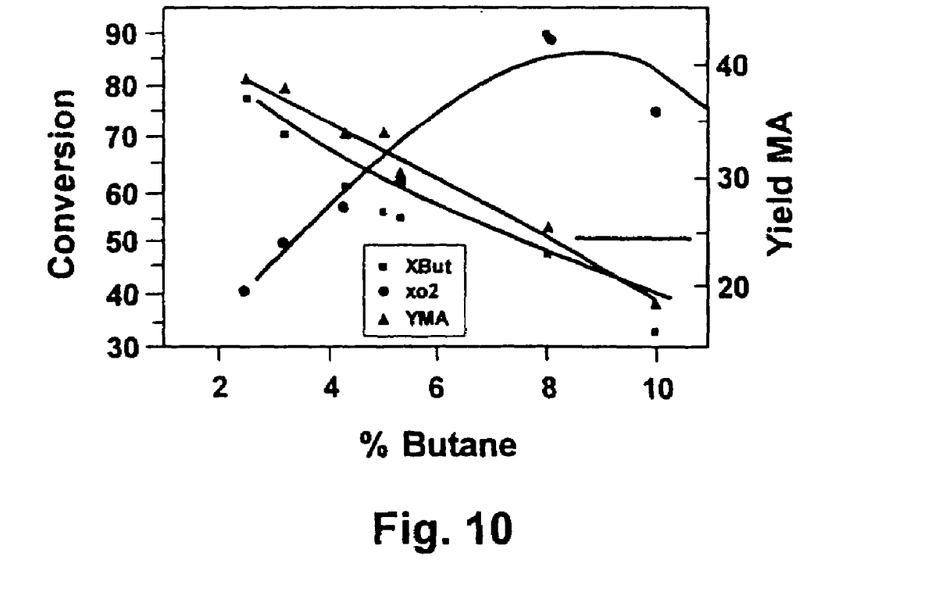
FIG. 10 is a graph showing oxygen conversion and yield based on percentage of butane according to an exemplary embodiment of the present invention.

In a reactor according to a further embodiment of the invention, the VPO catalyst is arranged in the space between the membrane and the stainless steel shell. N-butane was introduced into shell side and the oxygen into tube side of the reactor tube. Oxygen permeates thereby outwardly from tube side to shell side and the reactor is reference as Outward Flow Reactor (OFR). As obvious from FIG. 10, it was possible to reach a high oxygen conversion and still maintain a good MA selectivity. MA yields obtained by the OFR membrane reactor was about 30% with 5% butane. A proper introduction of oxygen, MA yields close to 30% can be obtained even with 10% butane in the feed.

EXAMPLE 7

Figure 11:
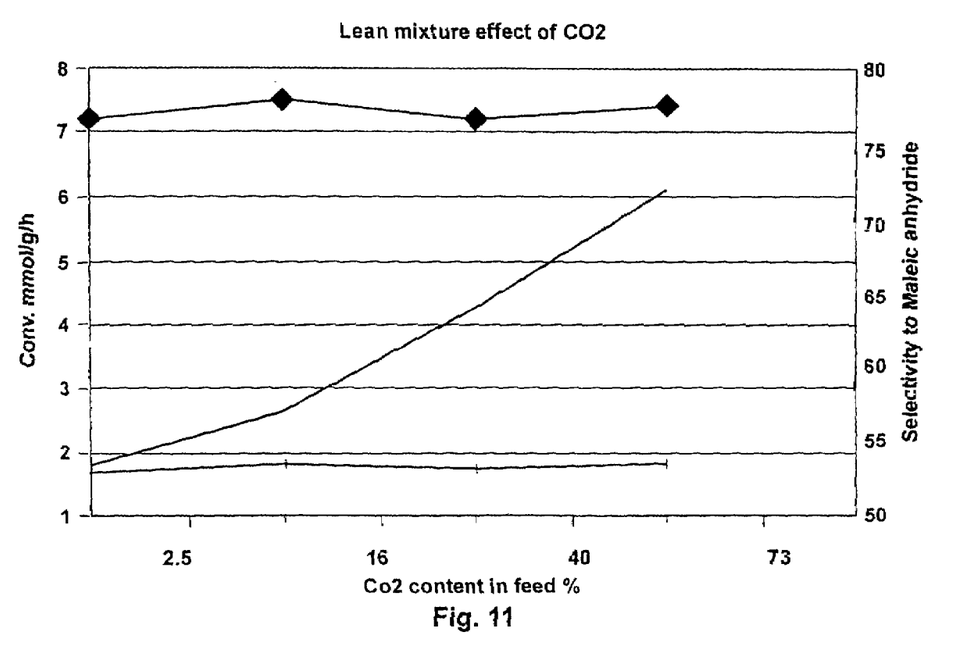
FIG. 11 is a graph illustrating selectivity in relation to $CO_2$ concentration according to an exemplary embodiment of the present invention.

The effect of feeding a mixture containing CO$_2$ to a fixed bed of VPO catalyst was tested at rich butane (20%) and lean (2.5%) butane concentration. The results show a clear increase in MA selectivity when the CO$_2$ content in the feed was increased (FIG. 11). The impact of CO$_2$ was higher with the butane-rich mixture than with the butane-lean: an increase in selectivity of 20% in the first case and only 5% in the second case was observed. Only small changes in butane conversion were obtained with CO$_2$.

EXAMPLE 8

A process according to a specific embodiment of the invention is based on the above described membrane technology. n-butane and oxygen react exothermically to maleic anhydride according to the following reaction scheme:

(1)

Additionally, side reactions are taking place according to the following reactions:

The above synthesis may be carried out in an IMR reactor according to a specific embodiment of the invention.

The dimensions of the membrane tube were: length=2 m; internal diameter=1"; thickness=0.78", the fix-bed reactor volume is approximately 1015 cm$^3$ with about 1830 g of VPO catalyst.

The reactor system included an inert membrane reactor with the tube dimensions given above. The reactor was operated by addition of one of the reactants (oxygen) and by heat removal and temperatures control of the reactor. One of the reactants was used as fluidization agent for particles of for example sand. The fluidised bed was arranged on shell side of the membrane tubes to remove heat from walls of the membrane tubes. The pressure on shell side was higher than tube side; thus, a flow of the reactant(s) from the fluidised bed to the reaction zone inside the tubes allowed control of concentration of the reactant(s). Thereby, the temperature of the fluidised bed was maintained below the temperature of the reaction zone and the flow from the fluidised bed to the reaction zone, so that the temperature can be adjusted in the reaction zone.

Use of $CO_2$ as carrier gas increased selectivity of the reaction to maleic anhydride.

Below are listed further process conditions and reactor dimensions employed in this example.

The ratio between the shell and tube area was 2.7. Oxygen content at the high-pressure side inlet to the reactor was controlled at 86% implying a recycle to makeup ratio of 2.6.

Oxygen was introduced into the membrane reactor at a velocity of 5 cm/s to fluidise the sand particles.

The fluidised bed and oxygen back mixing result in a substantial constant temperature of the oxygen stream throughout the entire reactor.

Diffusion through the membrane tubes was adjusted in such a manner that the reactor effluent at the low pressure side had an oxygen content of 5%.

Content of n-butane at reactor inlet was maintained at 5% by adjusting the n-butane fed to recycle ratio.

The n-butane feed was controlled to achieve a production of 50.000 MTPY maleic anhydride.

| Feedstocks | | |
|---|---|---|
| n-butane | | |
| Pressure, kg/cm² g | | 2.9 |
| Temperature, ° C. | | 25 |
| Composition | | 100% |
| Oxygen | | |
| Pressure, kg/cm² g | | 5 |
| Temperature, ° C. | | 25 |
| Composition (mole %): | $O_2$ | 95 |
| | $N_2$ | 1.9 |
| | Ar | 3.1 |
| Product | | |
| Maleic Anhydride | | |
| Pressure, kg/cm² g | | 0.7 |
| Temperature, ° C. | | 50 |
| Composition (mole %): | $C_4H_2O_3$ | 13.76 |
| | $H_2O$ | 86.24 |

EXAMPLE 9

A process according to a specific embodiment of the invention is based on the above described membrane technology. Propane and oxygen react exothermically to propylene and water according to the following reaction scheme:

$$C_3H_8 + 0.5\ O_2 \longrightarrow C_3H_6 + H_2O$$

Several side reactions occur according to the following reaction scheme:

$$C_3H_8 + 5\ O_2 \longrightarrow 3\ CO_2 + 4\ H_2O$$
$$C_3H_8 + 3.5\ O_2 \longrightarrow 3\ CO + 4\ H_2O$$

The above synthesis may be carried out in the above-described IMR reactor.

The dimensions of the membrane tube are: length=2 m; internal diameter=1"; thickness=0.78"; the fix-bed reactor volume is approximately 1015 cm³ with about 1800 g of vanadium magnesium oxide catalyst (VMgO).

The reactor system comprised an inert membrane reactor with tube dimensions as given above. The reactor was operated with addition of one of the reactants (oxygen) and at heat removal and temperature control of the reactor. One of the reactants was used as a fluidisation agent for particles of for example sand. The fluidised sand bed was arranged at shell side of the membrane tubes to remove the heat from walls of the membrane tubes. The pressure on the shell side was higher than the pressure on the tube side. Flow of the reactant(s) from the fluidised bed to the reaction zone inside the tubes allowed control of concentration of the reactant(s). The temperature of the fluidised bed was below the temperature of the reaction zone. The flow from the fluidised bed to the reaction zone controlled temperature in the reaction zone.

Further process conditions and reactor dimensions employed in the above process were:

The ratio between the shell and tube area was 2.7.

Oxygen content at the high-temperature side inlet to the reactor was 34%. Oxygen was introduced into the membrane reactor at a velocity of 0.2 m/s to fluidise the sand particles.

The fluidised bed and oxygen back mixing gave a substantially constant temperature of the oxygen stream throughout the entire reactor.

| Feedstocks | | |
|---|---|---|
| Propane | | |
| Pressure, kg/cm² g | | 2 |
| Temperature, ° C. | | 25 |
| Composition | | 100% |
| Oxygen | | |
| Pressure, kg/cm² g | | 3 |
| Temperature, ° C. | | 25 |
| Composition (mole %): | $O_2$ | 100. |
| Product | | |
| Propylene | | |
| Pressure, kg/cm² g | | 0.75 |
| Temperature, ° C. | | 60 |
| Composition (mole %): | | Propylene 100% |

The invention claimed is:

1. Process for the oxidative conversion of hydrocarbons by contacting a hydrocarbon-containing process gas with oxygen or oxygen-containing gas in presence of a catalyst active in the oxidation of the hydrocarbon, the process comprising the steps of:

passing a process gas containing the hydrocarbon through a reaction zone with the catalyst;

introducing the oxygen or oxygen-containing gas divided into a plurality of substreams successively and gradually into the reaction zone;

within the reaction zone reacting the process gas continuously with the oxygen or the oxygen-containing gas; and withdrawing from the reaction zone a product gas containing oxidized hydrocarbon compound and carbon monoxide, wherein heat is transported from the reaction zone by means of surrounding the reaction zone with a bed of inert particulate heat transfer material fluidized by the oxygen or the oxygen-containing gas.

2. Process of claim 1, wherein the hydrocarbon comprises n-butane or propane.

3. Process of claim 1, wherein the process gas contains at least 20% by volume of an inert gas.

4. Process of claim 3, wherein the inert gas is carbon dioxide.

5. Process of claim 4, wherein at least part of the carbon dioxide is obtained by oxidation of carbon monoxide in the product gas.

6. Process of claim 1, wherein the inert particulate heat transfer material is sand.

* * * * *